(12) United States Patent
Bille

(10) Patent No.: US 6,966,905 B2
(45) Date of Patent: Nov. 22, 2005

(54) EYE POSITION CONTROL MONITOR FOR LASER VISION CORRECTION

(75) Inventor: Josef Bille, Heidelberg (DE)

(73) Assignee: 20/10 Perfect Vision Optische Geraete GmbH, Heidelberg (DE)

( * ) Notice: Subject to any disclaimer, the term of this patent is extended or adjusted under 35 U.S.C. 154(b) by 0 days.

(21) Appl. No.: 10/718,980

(22) Filed: Nov. 20, 2003

(65) Prior Publication Data

US 2005/0113813 A1   May 26, 2005

(51) Int. Cl.$^7$ .............................................. A61F 9/007
(52) U.S. Cl. ............................ 606/5; 128/898; 606/4
(58) Field of Search ............................. 128/898; 606/5

(56) References Cited

U.S. PATENT DOCUMENTS

| | | | |
|---|---|---|---|
| 4,287,410 A | | 9/1981 | Crane et al. |
| 4,391,275 A | | 7/1983 | Fankhauser et al. |
| 4,443,075 A | | 4/1984 | Crane |
| 4,702,575 A | | 10/1987 | Breglia |
| 4,718,418 A | | 1/1988 | L'Esperance, Jr. |
| 4,848,340 A | | 7/1989 | Bille et al. |
| 4,881,808 A | * | 11/1989 | Bille et al. .................. 351/221 |
| 4,891,043 A | | 1/1990 | Zeimer et al. |
| 4,903,695 A | | 2/1990 | Warner et al. |
| 4,905,711 A | | 3/1990 | Bennett et al. |
| 5,108,412 A | | 4/1992 | Krumeich et al. |
| 5,283,598 A | * | 2/1994 | McMillan et al. .......... 351/212 |
| 5,336,215 A | | 8/1994 | Hsueh et al. |
| 5,549,632 A | * | 8/1996 | Lai ................................. 606/5 |
| 5,752,950 A | * | 5/1998 | Frey et al. ..................... 606/12 |
| 5,865,832 A | * | 2/1999 | Knopp et al. .................. 606/10 |
| 6,280,436 B1 | * | 8/2001 | Freeman et al. ............... 606/5 |
| 6,299,307 B1 | * | 10/2001 | Oltean et al. ................ 351/210 |
| 6,540,353 B1 | | 4/2003 | Dunn |
| 6,579,282 B2 | * | 6/2003 | Bille et al. ..................... 606/5 |
| 6,585,723 B1 | * | 7/2003 | Sumiya .......................... 606/5 |
| 6,666,857 B2 | * | 12/2003 | Smith .......................... 606/12 |
| 2003/0009156 A1 | * | 1/2003 | Levine .......................... 606/5 |
| 2003/0100893 A1 | | 5/2003 | Bille |
| 2004/0059321 A1 | * | 3/2004 | Knopp et al. ................. 606/10 |
| 2004/0199150 A1 | * | 10/2004 | Lai ................................. 606/5 |

* cited by examiner

Primary Examiner—Henry M Johnson, III
(74) Attorney, Agent, or Firm—Nydegger & Associates

(57) ABSTRACT

A system for spatially stabilizing a base point on the optical axis of a patient's eye, for photoablation of the cornea, includes an optical element for identifying the base point. The system also includes an illumination source which is a fixation point for the eye. Movement of the illumination source induces a saccadic movement of the eye wherein the optical axis of the eye moves from a first orientation to a second orientation. Following the saccadic movement of the eye there is a latency period during which the base point, and hence the eye, is substantially stabilized. Movement of the light source is timed to coincide the latency period with the resting period of the patient's heartbeat sequence, and the relaxation period of the patient's respiration cycle. During the latency period, photoablation is accomplished by directing a train of laser pulses from a laser source into the corneal tissue.

20 Claims, 1 Drawing Sheet

EYE POSITION CONTROL MONITOR FOR LASER VISION CORRECTION

FIELD OF THE INVENTION

The present invention pertains generally to systems and methods for ophthalmic laser surgery. More particularly the present invention pertains to the photoablation of corneal tissue by a continuous train of laser pulses during time periods when the eye is in a relatively stable position. The present invention is particularly, but not exclusively, useful as a system for spatially stabilizing a selected base point on the optical axis of a patient's eye for photoablation of the corneal tissue by inducing a saccadic movement of the eye at a predetermined moment in time.

BACKGROUND OF THE INVENTION

The human eye is a very delicate, complex, and imperfect optical system. Over much of the last 250 years, techniques for measuring and correcting the optical impairments of the eye have been limited to addressing nearsightedness or farsightedness, and the corresponding cylindrical refractive errors. The human eye, however, also shows higher order refractive errors, or so-called "higher aberrations". As the light levels decrease, the quality of a person's vision is affected more by the higher aberrations than by cylindrical refractive errors. For example, pupils dilate in twilight situations in order to project more light onto the retina of the eye. As a result, light rays pass through the peripheral regions in the eye where greater refractive errors are present. Therefore, even a person with normal 20/20 vision has a decreased visual acuity under critical illumination conditions. By accessing and correcting the higher order refractive errors, visual performance can be significantly improved.

Wavefront analysis is a developing technology which has been shown to significantly enhance operational aspects of refractive surgery on the human eye. In particular, as the eye focuses on an image, flat sheets of light (wavefronts) passing through the eye are distorted by the imperfect refractive medium. Hence, a wavefront will tend to distort on it's way through an irregular cornea or lens. Simple refractive errors, like nearsightedness or farsightedness, normally result in a simple bowl-like, symmetrical wavefront distortion. Higher order aberrations, however, can yield a more complex, non-symmetrical distortion of the originally flat wavefront, which is unique for every person's eye. These wavefront distortions will then lead to blurred optical imaging of viewed scenes.

Recent advances in integrated wavefront sensing technology allow for the measurement of simple refractive errors, as well as for the measurement of higher order aberrations. These measurements are now performed with previously unknown precision and speed. Thus, the refractive power of an individual's eye can be spatially measured over the diameter of the pupil, and based on the measured individual wavefront distortions, a person's visual acuity can be improved. When eyeglasses are inadequate to make the necessary improvements, refractive surgery may be necessary. These improvements can be accomplished in one of several ways.

One approach to vision correction by refractive surgery involves the external pre-compensation of errors in the wavefront using adaptive optics. By reflecting the wavefront of a viewed scene at a deformable active mirror in the adaptive optics, a distortion can be introduced which inversely matches the wavefront distortion of the eye. The wavefront distortion of the eye and the active mirror then cancel each other, and the patient sees a perfectly sharp image without higher order refractive errors. Based on this phenomenon, reliable micro-mechanical active mirrors can be used in a closed-loop system, where the measured distortions are directly converted into surface changes of the mirror. It happens that these distortions can be used for refractive surgery.

With refractive surgery, the corneal tissue is ablated using a focused laser beam. More specifically, this treatment can be based on individually measured wavefront aberrations, with tissue ablation permanently neutralizing the refractive errors of the patient's eye. A system for accomplishing tissue ablation is disclosed in U.S. Pat. No. 6,610,051, titled "A Device and Method for Performing Refractive Surgery", issued to Bille and assigned to the same assignee as the present application, i.e. 20/10 Perfect Vision Optische Geraete GmbH. Further, it is well known to those skilled in the art that accurate and precise refractive surgery requires the corneal tissue be photoablated when the eye is substantially stabilized or stationary. It is also well known that the eye is naturally stabilized following a saccadic movement of the eye.

Saccadic movements of the eye are the rapid, ballistic like movements of the eye used in scanning an observed scene. These movements are involuntary, and occur even when the eye is apparently fixed on a given object or fixation point. It is possible, however, to initiate a saccadic movement of the eye at a predetermined moment in time by moving a fixation point through an arc of about 5° (five degrees). After each such saccadic eye movement, there is a latency period of approximately 0.12 seconds when the eye is substantially stabilized.

For many reasons, it is desirable to perform photoablation of the corneal tissue when the eye is stabilized. Such stabilization is best assured if photoablation is accomplished during the latency period that follows a saccadic eye movement. It may be critical, therefore, to coordinate the laser procedure with the saccadic movement of the eye. It happens, however, that stabilization of the eye through only saccadic eye movement may not be adequate, in many instances, to allow for laser cutting. This is so because there are other physiological phenomena that may cause the eye to move. For example, the beating of a patient's heart, as well as the inhaling and exhaling associated with a respiration cycle, causes the eye to move. Obviously, either of these movements can prevent the accurate photoablation of the corneal tissue. Importantly, both of these physiological events are rhythmic in nature, and both include a period of non-activity.

In light of the above, it is an object of the present invention to provide a system for spatially stabilizing a selected base point on the optical axis of a patient's eye during the latency period following a saccadic eye movement. Another object of the present invention is to provide a system stabilizing the base point, following a saccadic movement of the eye, during the resting period in a heartbeat sequence, and during the relaxation period in a respiration cycle of the patient. Yet another object of the present invention is to provide a system for photoablating corneal tissue during the period of time when the base point, and hence the eye, is substantially stabilized. Still another object of the present invention is to provide a system for stabilizing a base point on the optical axis of the eye that is easy to use, relatively simple to manufacture, and comparatively cost effective.

SUMMARY OF THE INVENTION

The present invention is directed to a system for stabilizing a selected base point on an optical axis of a patient's eye. As contemplated by the present invention, the system includes an optical element for identifying the base point on the optical axis of the patient's eye. In addition, the optical element may be used to monitor changes in the relative position and stability of the base point, to determine a resting period in a heartbeat sequence of the patient, and a relaxation period in the patient's respiration cycle. The system also includes an illumination source which can be moved from a first position or orientation to a second position. In accordance with the present invention, the illumination source can be a light source which serves as a fixation point for the eye. Importantly, when the light source is moved between the first position and the second position, a saccadic movement of the eye ensues. Following the saccadic movement of the eye, there is a latency period during which the base point, and hence the eye, is substantially stabilized.

For the purposes of the present invention, a computer controller is in electronic communication with both the optical element and the light source. The computer controller monitors input data from the optical element regarding the position and stability of the base point along the optical axis. After processing the data, the computer controller moves the light source to coincide the latency period following the saccadic eye movement with the resting period of the heartbeat, and the relaxation period of the respiration cycle.

As contemplated by the present invention, the system also includes a power source and a laser source for generating a laser beam. In addition, a set of guidance optics focus the laser beam onto predetermined focal points within the cornea of the patient. Through this surgical process, the corneal tissue is photoablated in accordance with a predefined surgical pattern. An alignment device is used to verify the alignment of the optical axis immediately preceding each photoablation event. The alignment device may be one of any devices well known in the pertinent art, to include the confocal arrangement or the wavefront sensor of the optical element, or a device for detecting circular polarized light reflected off the retina.

In operation, a base point is identified along the optical axis of the eye. It happens that the base point can be identified using a confocal arrangement. For the purposes of the present invention, the confocal arrangement identifies the base point by ascertaining the focal spot of the specular reflectance of the light source from the anterior surface of the cornea. The identification of the base point occurs when the light source, and hence the optical axis of the eye, are in the first position.

When the light source is moved from the first position to the second position, a saccadic movement of the eye occurs. This saccadic movement realigns the optical axis of the eye with the light source. When the light source is subsequently moved back to the first position, a second saccadic eye movement takes place. During the latency period that follows the second saccadic eye movement, the base point is substantially stabilized. If the location of the base point is within an acceptable margin of error (i.e. ±20 μm), and the optical axis is properly aligned with the system as verified by the alignment device, photoablation may proceed. Stated differently, in the preferred embodiment of the present invention, photoablation of the corneal tissue occurs after the base point is stabilized in the first position, and the alignment of the optical axis is properly verified.

It can be appreciated by those skilled in the art that it is possible to photoablate corneal tissue with each saccadic movement of the eye. Thus, in an alternate embodiment of the present invention, photoablation occurs while the eye is stabilized, and the optical axis is aligned, in both the first and the second positions. To accurately determine both the first and the second positions of the eye, a wavefront sensor consisting of a wavefront analyzer and an active mirror can be used. The wavefront sensor can also be used to help define a new surgical pattern, as necessary, after each saccadic eye movement. As each new surgical pattern is defined, photoablation may proceed.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
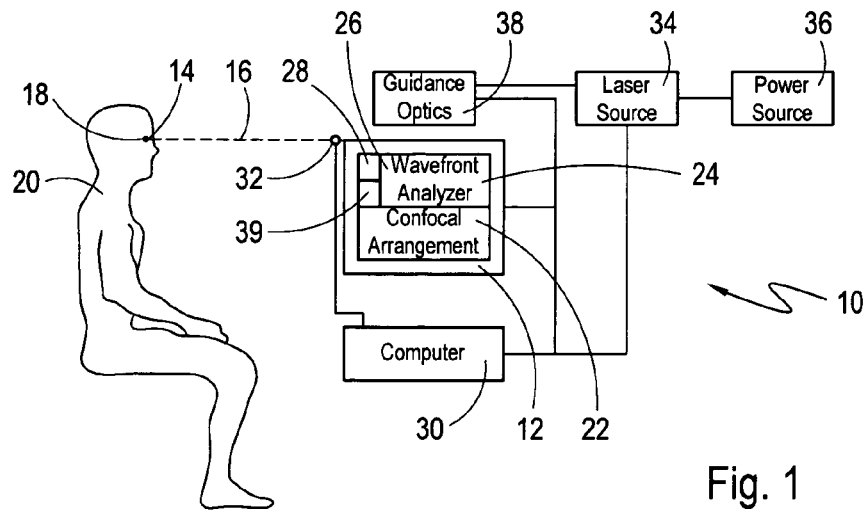
FIG. 1 is a schematic view of a system in accordance with the present invention for stabilizing and photoablating the corneal tissue of a patient's eye.

A system in accordance with the present invention is shown in FIG. 1 and generally designated 10. As shown in FIG. 1, the system 10 includes an optical element 12 for identifying a base point 14 on an optical axis 16 of the eye 18 of a patient 20. More specifically, the optical element 12 comprises a confocal arrangement 22 and a wavefront sensor 24. The wavefront sensor 24 further comprises a wavefront analyzer 26 and an active mirror 28. In one embodiment of the present invention, the confocal arrangement 22 is used to identify the base point 14 of the eye 18. In an alternate embodiment, the wavefront sensor 24, consisting of the wavefront analyzer 26 and active mirror 28, is used to identify the base point 14. The use of the confocal arrangement 22 or the wavefront sensor 24 is dictated by the operational mode of the system 10, as further described below. As shown in FIG. 1, the optical element 12 is in electronic communication with a computer controller 30.

As contemplated by the present invention, the confocal arrangement 22 may also be used to determine the resting period in a heartbeat sequence of the patient, and a relaxation period in the patient's respiration cycle. Specifically, the confocal arrangement 22 is used to optically monitor the movement of the base point 14 induced by each heartbeat or each breath. Using this data, the system 10 can then determine when the base point 14, and hence the eye 18, is substantially stationary and stable.

Still referring to FIG. 1, the system 10 includes an illumination source 32 which serves as a fixation point for the eye 18 of the patient 20. For the purposes of the present invention, the illumination source 32 may be any source of visible light known in the pertinent art. Importantly, the illumination or light source 32 is capable of being moved electronically, and the movement of the light source 32 is controlled by the computer controller 30.

An important aspect of the present invention is a laser source 34 which generates a train of laser pulses for photoablation of the corneal tissue. A power source 36 is in electronic communication with the laser source 34. As contemplated by the present invention, the laser source 34 works in concert with a set of guidance optics 38 to properly align the surgical laser. The guidance optics 38 direct the train of laser pulses toward a predetermined focal point within the cornea 40 (FIG. 2) of the eye 18. Of note, the laser source 34, the power source 36, and the guidance optics 38 are controlled by the computer controller 30.

As shown in FIG. 1, the system 10 includes an alignment device 39 for verifying the alignment of the optical axis 16 immediately prior to the photoablation event. The alignment device 39 may be the confocal arrangement 22 or the wavefront sensor 24 integral to the optical element 12, or it may be any type of device well known in the pertinent art. One such alignment device 39 is a sensor for detecting circular polarized light reflected from the retina.

Figure 2:
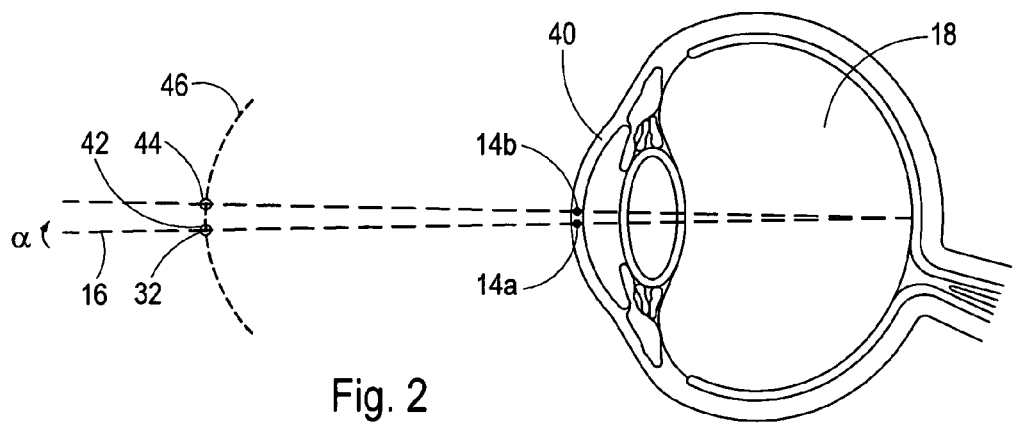
FIG. 2 is a schematic view of a human eye, an illumination source, and the optical axis of the eye.

In operation, the light source 32 is a fixation point for the eye 18 of the patient 20. As the eye 18 fixates on the light source 32, the optical axis 16 aligns with the light source 32, as shown in FIGS. 1 and 2. In one embodiment of the present invention, the confocal arrangement 22 identifies the base point 14, which is located along the optical axis 16 of the eye 18. More specifically, the confocal arrangement 22 ascertains the focal point of the specular reflectance of the light source 32, as measured from the surface of the cornea 40 of the eye 18. For the purposes of the present invention, the focal spot is the base point 14.

Still referring to FIG. 2, the light source 32 is moved from a first position 42 to a second position 44, through some angle "alpha" along an arc 46 which is centered on the optical axis 16. As contemplated by the present invention, the angle "alpha" is approximately 5°. After the light source 32 is moved from a first position 42 to a second position 44, a corresponding saccadic movement of the eye 18 realigns the optical axis 16 with the light source 32. Correspondingly, the base point 14 changes from an initial position 14a, when the light source 32 is in the first position 42, to a subsequent position 14b, after the light source 32 has moved to the second position 44. Because the eye 18 rotates at a rate of about 600°/sec, it takes approximately $5/600^{th}$ of a second for the optical axis 16 to move from the first position 42 to the second position 44. Following this saccadic movement of the eye 18, there is a latency period, "$t_l$", during which the base point 14, and hence the eye 18, is substantially stabilized. The duration of the latency period following a saccadic movement of the eye 18 is about 0.12 seconds. After the initial movement of the light source 32, from a first position 42 to a second position 44, the process is repeated in reverse. Once again, there is a saccadic movement of the eye 18 followed by a latency period "$t_l$".

Figure 3:
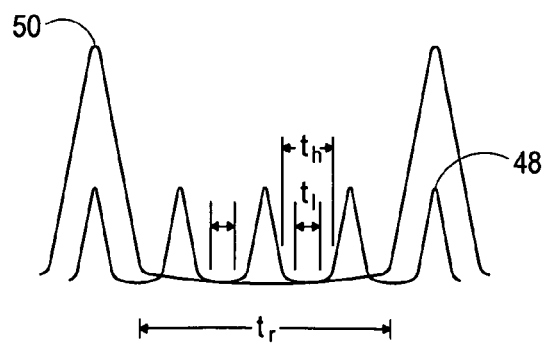
FIG. 3 is a graphical representation of the z-direction displacement of the eye as a function of time.

Concurrent with the movement of the light source 32, the computer controller 30 is receiving data from the optical element 12 regarding the relative "z-direction displacement" of the base point 14. Referring now to FIG. 3, it can be seen that there is a short duration, z-direction displacement 48 of the base point 14 induced by a heartbeat. The magnitude of the displacement 48 is approximately 10 microns, and the duration of the displacement 48 is on the order of tenths of a second. The periodicity or frequency of the displacement 48 is typically one beat or displacement 48 per second. Between each displacement 48 there is a resting period "$t_h$". Still referring to FIG. 3, the displacement 50 caused by the respiration cycle of the patient 20 is much greater than the displacement 48 caused by a heartbeat. The respiratory displacement 50 is approximately 200 microns. Likewise, the duration of the respiratory displacement 50 is longer than the duration of the heartbeat displacement 48, and is typically on the order of one second. The periodicity of the respiratory displacement 50 is once every four seconds, which is to say the relaxation period "$t_r$" between respiratory displacements 50 is about four seconds. It can be understood, therefore, that the duration of the relaxation period "$t_r$", as shown in FIG. 3, is greater than the duration of the resting period, "$t_h$". In addition, the durations of both the relaxation period "$t_r$" and the resting period "$t_h$" are greater than the duration of the latency period "$t_l$" that follows a saccadic movement of the eye 18. As such, the latency period "$t_l$" is the critical time window. The eye 18 is most stable, therefore, during the period of time when the relaxation period "$t_r$", the resting period "$t_h$", and the latency period "$t_l$" coincide.

It can be appreciated by those skilled in the art that photoablation of the corneal tissue should not occur during periods of eye 18 displacement, as shown in FIG. 3. Additionally, photoablation should not occur if the optical axis 16 is not properly aligned with the system 10. As contemplated by the present invention, the computer controller 30 coordinates the movement of the light source 32 between the first position 42 to the second position 44, to ensure that the periods of latency, rest and relaxation ($t_l$, $t_h$, $t_r$) coincide. In one embodiment of the present invention, photoablation only occurs during the latency period "$t_l$" following movement of the eye 18 from the second position 44 back to the first position 42. Stated differently, the operational mode may be represented as: move (from the first position 42 to the second position 44)—fixate—move (back to the first position 42)—fixate—verify alignment—ablate. After the second saccadic movement of the eye 18, back to the first position 42, the eye 18 of the patient 20 is substantially stabilized. During this period of stabilization, the position of the base point 14 and the alignment of the optical axis 16 are confirmed. If the location of the base point 14 is within an acceptable margin of error (i.e. ±20 µm), and the alignment of the optical axis 16 is properly verified by the alignment device 39, photoablation may proceed. In the preferred embodiment of the present invention, photoablation is accomplished by a laser source 34 generating a train of laser pulses. For each surgical disruption of the corneal tissue, the train of pulses is about 1500 pulses. If, however, the margin of error is too great, a new base point 14 must be identified using the optical element 12. Once the new base point 14 is defined, the process of moving the light source 32 from a first position 42 to a second position 44 and back again is repeated. Following the saccadic movement of the eye 18 back to a first position 42, photoablation may occur.

It may be understood by those skilled in the art, that an alternate embodiment of the present invention includes photoablation of corneal tissue with each saccadic movement of the eye 18. Importantly, in this alternate embodiment of the present invention, the confocal arrangement 22 is not used to identify the base point 14. Of note, when the light source 32 is moved five degrees (5°) in either direction along the arc 46, the corresponding lateral distance on the surface of the cornea 40 is about 0.3 mm. It happens that with movements in excess of 0.2 mm, the confocal arrangement 22 is not the optimal device for identifying the base point 14. Consequently, when it is necessary to identify the position of the eye 18 after each saccadic movement, the wavefront sensor 24 is used. Using the wavefront sensor 24 to identify the position of the eye 18 allows for photoablation with each saccadic movement of the eye 18. This operational mode of "move-fixate-verify-ablate, move-fixate-verify-ablate" can be repeated as the light source 32, and hence the optical axis 16 of the eye 18, moves back and forth between the first position 42 and second position 44. In addition to identifying the position of the eye 18, the wavefront sensor 24 can be used to help define a new surgical pattern for photoablation when procedural conditions require such a pattern.

While the particular Eye Position Control Monitor for Laser Vision Correction as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for spatially stabilizing a selected base point on the optical axis of an eye of a patient, following a saccadic movement of said eye, which comprises:
    an optical means for identifying said base point; and
    an illumination means, with means for moving illumination from said illumination means from a first position to a second position, at a distance from said eye, for causing said optical axis of said eye to respectively move from a first orientation to a second orientation to stimulate a saccadic movement of said eye, with a subsequent latency period wherein said selected base point is substantially stabilized.

2. A system as recited in claim 1 further comprising:
    a means for determining a resting period in a heartbeat sequence and a relaxation period in a respiration cycle of said patient; and
    a computer controller in electronic communication with said determining means for coinciding said resting period and said relaxation period with said latency period to further substantially stabilize said base point during said latency period.

3. A system as recited in claim 2 wherein said determining means is a confocal arrangement.

4. A system as recited in claim 1 wherein said illumination means is a light source for establishing a fixation point and further wherein said fixation point is moved by said moving means through an arc of approximately five degrees to move said optical axis of said eye from said first orientation to said second orientation.

5. A system as recited in claim 1 further comprising:
    a laser source for generating a train of laser pulses; and
    a guidance optic for directing said train of laser pulses toward said eye for photoablating corneal tissue of said eye during said latency period.

6. A system as recited in claim 5 which further comprises a means for verifying the alignment of the optical axis of the eye immediately prior to said photoablating of said corneal tissue.

7. A system as recited in claim 5 wherein said train of laser pulses is approximately 1500 pulses.

8. A system as recited in claim 1 wherein said optical means includes a confocal arrangement to ascertain the focal point of the specular reflection of said illumination means from the anterior surface of said eye.

9. A system as recited in claim 1 further comprising a wavefront sensor to identify said base point.

10. A system as recited in claim 9 wherein the wavefront sensor consists of:
    a wavefront analyzer; and
    an active mirror.

11. A method for spatially stabilizing a selected base point on an optical axis of an eye of a patient following a saccadic movement of said eye which comprises the steps of:
    identifying a base point on said optical axis of said eye; and
    moving an illumination means to cause said optical axis of said eye to move from a first orientation to a second orientation, for stimulating a saccadic movement of said eye, with a subsequent latency period wherein said selected base point is substantially stabilized.

12. A method as recited in claim 11 further comprising the steps of:
    determining a resting period in a heartbeat sequence of the patient;
    determining a relaxation period in a respiration cycle of the patient; and
    coinciding said resting period and said relaxation period with said latency period to further substantially stabilize said base point during said latency period.

13. A method as recited in claim 12 wherein said resting period and said relaxation period are determined using a confocal arrangement.

14. A method as recited in claim 11 wherein said illumination means is a light source for establishing a fixation point and further wherein said fixation point is moved through an arc of approximately five degrees to move said optical axis of said eye from said first orientation to said second orientation.

15. A method as recited in claim 11 further comprising the steps of:
    generating a train of laser pulses; and
    directing said train of laser pulses into said eye during said latency period for photoablating corneal tissue of said eye.

16. A method as recited in claim 15 wherein said train of laser pulses is approximately 1500 pulses.

17. A method as recited in claim 15 which further comprises the step of verifying the alignment of the optical axis of the eye immediately prior to said photoablating of said corneal tissue.

18. A method as recited in claim 11 wherein said base point is identified using a confocal arrangement to ascertain the focal point of the specular reflection of said illumination means from the anterior surface of said eye.

19. A method as recited in claim 11 wherein the said base point is identified using a wavefront sensor.

20. A method as recited in claim 19 wherein said wavefront sensor consists of:
    a wavefront analyzer; and
    an active mirror.

* * * * *